(12) United States Patent
Nishioka et al.

(10) Patent No.: US 9,920,954 B2
(45) Date of Patent: Mar. 20, 2018

(54) HEATING TOOL

(71) Applicant: Kobayashi Pharmaceutical Co., Ltd., Osaka-shi (JP)

(72) Inventors: Daisuke Nishioka, Osaka (JP); Yuki Yasuda, Osaka (JP); Hiromichi Tanaka, Osaka (JP)

(73) Assignee: Kobayashi Pharmaceutical Co., Ltd., Osaka-shi (JP)

( * ) Notice: Subject to any disclaimer, the term of this patent is extended or adjusted under 35 U.S.C. 154(b) by 443 days.

(21) Appl. No.: 14/375,988

(22) PCT Filed: Jan. 31, 2013

(86) PCT No.: PCT/JP2013/052177
§ 371 (c)(1),
(2) Date: Jul. 31, 2014

(87) PCT Pub. No.: WO2013/115306
PCT Pub. Date: Aug. 8, 2013

(65) Prior Publication Data
US 2014/0345595 A1    Nov. 27, 2014

(30) Foreign Application Priority Data

Jan. 31, 2012 (JP) .................................. 2012-018368
Jan. 30, 2013 (JP) .................................. 2013-015526

(51) Int. Cl.
*F24J 1/00* (2006.01)
*A61F 7/03* (2006.01)
(Continued)

(52) U.S. Cl.
CPC ................. *F24J 1/00* (2013.01); *A61F 7/034* (2013.01); *A61F 2007/0003* (2013.01);
(Continued)

(58) Field of Classification Search
CPC .............. A61F 7/034; A61F 2007/0003; A61F 2007/0011; A61F 2007/0023;
(Continued)

(56) References Cited

U.S. PATENT DOCUMENTS

2004/0149732 A1    8/2004    Usui et al.
2006/0154006 A1*    7/2006    Usui ....................... A61F 7/034
                                                                                                              428/34.1
(Continued)

FOREIGN PATENT DOCUMENTS

CN    101338182 A    1/2009
JP    57-119753 A    7/1982
(Continued)

OTHER PUBLICATIONS

Supplementary European Search Report dated Oct. 6, 2015 for EP Patent Application No. 13743049.2.
(Continued)

*Primary Examiner* — Alfred Basichas
(74) *Attorney, Agent, or Firm* — Locke Lord LLP; James E. Armstrong, IV; Nicholas J. DiCeglie, Jr.

(57) ABSTRACT

Provided is a superior heating tool which is capable of producing desired aromatic properties upon usage even after being stored for a long period of time. A heating tool comprising: an exothermic composition containing an oxidation accelerator having an iodine adsorption of not higher than 500 mg/g, an oxidizable metal powder, and water; and a fragrance, wherein at least the exothermic composition is housed in a container bag having air permeability.

16 Claims, 1 Drawing Sheet

(51) Int. Cl.
*A61F 7/00* (2006.01)
*A61F 7/02* (2006.01)

(52) U.S. Cl.
CPC . *A61F 2007/003* (2013.01); *A61F 2007/0011* (2013.01); *A61F 2007/0023* (2013.01); *A61F 2007/0024* (2013.01); *A61F 2007/0032* (2013.01); *A61F 2007/0036* (2013.01); *A61F 2007/0042* (2013.01); *A61F 2007/0226* (2013.01); *A61F 2007/0233* (2013.01)

(58) Field of Classification Search
CPC ........ A61F 2007/0233; A61F 2007/003; A61F 2007/0032; A61F 2007/0036; A61F 2007/0042; A61F 2007/0226; A61F 2007/0024; F24J 1/00
See application file for complete search history.

(56) References Cited

U.S. PATENT DOCUMENTS

| | | | |
|---|---|---|---|
| 2008/0206549 | A1 | 8/2008 | Dodo |
| 2015/0211766 | A1* | 7/2015 | Yasuda ............... A61F 7/034 126/263.06 |
| 2016/0174569 | A1* | 6/2016 | Maruyama ............ A01M 31/06 43/3 |

FOREIGN PATENT DOCUMENTS

| | | |
|---|---|---|
| JP | 05-194952 A | 8/1993 |
| JP | 05-279595 A | 10/1993 |
| JP | 2000-060887 A | 2/2000 |
| JP | 2001-218816 A | 8/2001 |
| JP | 2002-204833 A | 7/2002 |
| JP | 2004-073828 A | 3/2004 |
| JP | 2004-180959 A | 7/2004 |
| JP | 2006-223851 A | 8/2006 |
| JP | 2007-154105 A | 6/2007 |
| JP | 4093348 B2 | 6/2008 |
| JP | 2009-035723 A | 2/2009 |
| JP | 2009-062250 A | 3/2009 |
| JP | 2010-022405 A | 2/2010 |
| JP | 2010-051690 A | 3/2010 |
| JP | 2011-160885 A | 8/2011 |
| WO | WO-2006/006656 A1 | 1/2006 |

OTHER PUBLICATIONS

International Search Report dated Feb. 26, 2013, issued for PCT/JP2013/052177.
Office Action issued in corresponding Japanese Patent Application No. JP 2013-015526, dated Aug. 1, 2017.
Adsorption of Iodine by Carbon Black (2), Nippon Gomu Kyokaishi, 1962, vol. 35, No. 8, pp. 578-582.
Carbonization and activation techniques for production of carbonaceous adsorbent, Tanso, 2004, No. 211, pp. 21-29.

* cited by examiner

HEATING TOOL

TECHNICAL FIELD

The present invention relates to a heating tool. More specifically, the present invention relates to a heating tool capable of producing excellent aromatic properties even after being stored for a long period of time.

BACKGROUND ART

Hitherto, disposable hand warmers have been frequently used since they are highly portable, safe, convenient, etc., as a warming tool for the body, and also economical. In a typical disposable hand warmer, an exothermic composition that generates heat in the presence of air is used, and a heat keeping effect is produced through this heat generating mechanism. Hitherto, perfuming of heating tools utilizing the heat generating mechanism, such as disposable hand warmers, has been reported.

For example, Patent Literature 1 discloses a fragrance inclusion body. In the fragrance inclusion body an inclusion body formed of a material having air tightness is divided into two parts by a shielding sheet, and a fragrance impregnated body is housed in one of the two parts, while an exothermic composition is housed in the other. Provided on both sides of the divided inclusion body are a vent, a sealing material covering the vent, and a pressure-sensitive adhesive layer interposed between the sealing material and the inclusion body. When the pressure-sensitive adhesive layer is peeled off for usage, aroma is released using the heat generating mechanism to be enjoyed. Such a fragrance inclusion body needs to be covered through adherence with adhesive strength weak enough to enable easy peeling by hand of the sealing material and the pressure-sensitive adhesive layer for usage. However, sufficient air tightness cannot be obtained with such a weak adhesive strength. Therefore, aromatic properties are lost during storage before usage, and desired aromatic properties cannot be obtained upon usage.

As an example in which air tightness is increased further, Patent Literature 2 discloses an aromatic tool including an aromatic bag in which an air-permeable inner bag containing agents and fragrances is sealed in an air-impermeable outer bag, a heating bag in which an air-permeable inner bag containing an exothermic composition which generates heat upon making contact with oxygen in the air is sealed in an air-impermeable outer bag, and an air-permeable package in which the inner bag of the aromatic bag and the inner bag of the heating bag can be placed. The aromatic bag and the heating bag are sealed separately in the air-impermeable outer bags to prevent contact with each other during storage. However, in this case, an extra work of opening each of the outer bags and then placing each of the inner bags in the air-permeable package becomes necessary upon usage. In addition, an economical disadvantage regarding the need to prepare an air-permeable package exists. Patent Literature 3 discloses a disposable hand warmer including: a hand warmer body in which a heating element is enclosed in a bag body having pores; a peeling sheet having air-impermeability, being stuck to a portion of the bag body in an easily peelable manner to block the pores, and being peeled off upon usage; and a nonwoven fabric being impregnated with an aromatic agent and stuck to the bag body or the peeling sheet. However, as in Patent Literature 3, the disposable hand warmer requires the extra work of peeling off the peeling sheet etc., upon usage.

As an example in which such extra work is not required, for example, Patent Literature 4 discloses including agents or fragrances on the surface of a hitherto-known disposable hand warmer, and promoting the volatilization and diffusion of these agents or fragrances through utilization of the heat generating mechanism of the disposable hand warmer. However, since activated carbon is used in the exothermic composition in a typical disposable hand warmer, when agents or fragrances are contained on the surface of the disposable hand warmer as in this case, handling becomes easy, but the agents or fragrances are adsorbed or altered by the activated carbon in the exothermic composition during storage, and sufficient volatilization and diffusion effects cannot be obtained.

Patent Literature 5 discloses a heating tool perfumed with a fragrance composition containing specific components. The heating tool includes: a heating portion including an oxidizable metal and activated carbon; and a bag body having air permeability and housing the heating portion. However, in Patent Literature 5, from the perspective of sustaining the aromatic properties, the types of usable fragrances are greatly limited.

CITATION LIST

Patent Literature

PTL 1: JPS57-119753A
PTL 2: JP2004-180959A
PTL 3: JP2010-022405A
PTL 4: JP2001-218816A
PTL 5: JP2010-051690A

SUMMARY OF INVENTION

Technical Problem

For these reasons, an object of the present invention is to provide a superior heating tool which is capable of producing desired aromatic properties upon usage even after being stored for a long period of time.

Solution to Problem

The present inventors have conducted extensive research to solve the above problem, and as a result found that in a heating tool, by using an oxidation accelerator having an iodine adsorption of not higher than 500 mg/g, even in the case where a fragrance for perfuming the heating tool and an exothermic composition coexist in contact with each other, excellent aromatic properties can be obtained upon usage after long-term storage, and exothermic effects sufficient for a heating tool can be obtained. The present invention has been accomplished by conducting further research based on such findings.

That is, the present invention provides the inventions listed below.

Item 1. A heating tool comprising: an exothermic composition containing an oxidation accelerator having an iodine adsorption of not higher than 500 mg/g, an oxidizable metal powder, and water; and a fragrance, wherein at least the exothermic composition is housed in a container bag having air permeability.

Item 2. The heating tool according to item 1, wherein the exothermic composition further contains a water soluble salt and/or a water-retaining agent.

Item 3. The heating tool according to item 1 or 2, wherein the proportion of the oxidation accelerator in the exothermic composition is 1 to 30 wt %.
Item 4. The heating tool according to any one of items 1 to 3, wherein the fragrance is contained in an amount of 0.0001 to 5 parts by weight per 100 parts by weight of the exothermic composition.
Item 5. The heating tool according to any one of items 1 to 4, wherein the fragrance is contained in an amount of 0.0003 to 500 parts by weight per 100 parts by weight of the oxidation accelerator in the exothermic composition.
Item 6. The heating tool according to any one of items 1 to 5, wherein the oxidation accelerator is at least one substance selected from the group consisting of carbon black, graphite, activated carbon, coal, charcoal, bamboo charcoal, acetylene black, and waste coffee grounds charcoal.
Item 7. The heating tool according to any one of items 1 to 6, wherein the iodine adsorption of the oxidation accelerator is not higher than 400 mg/g.
Item 8. The heating tool according to any of items 1 to 7, wherein the oxidation accelerator has electrical conductivity.
Item 9. The heating tool according to any one of items 1 to 8, the heating tool comprising: an electrical conductive oxidation accelerator having an iodine adsorption of not higher than 400 mg/g; an oxidizable metal powder; water; a water soluble salt; and a water-retaining agent.
Item 10. The heating tool according to any one of items 1 to 9, wherein the fragrance is further housed in the container bag having air permeability.
Item 11. The heating tool according to any one of items 1 to 10, wherein the fragrance is supported on a carrier.
Item 12. A use of, for producing a heating tool containing a fragrance, an exothermic composition containing an oxidation accelerator having an iodine adsorption of not higher than 500 mg/g, an oxidizable metal powder, and water.
Item 13. The use according to item 12, wherein the fragrance, the heating tool, and/or the exothermic composition have/has the feature according to any one of items 1 to 11.
Item 14. A use of, for sustaining aromatic properties derived from a fragrance in a heating tool containing the fragrance, an exothermic composition containing an oxidation accelerator having an iodine adsorption of not higher than 500 mg/g, an oxidizable metal powder, and water.
Item 15. The use according to item 14, wherein the fragrance, the heating tool, and/or the exothermic composition have/has the feature according to any one of items 1 to 11.
Item 16. A method for sustaining aromatic properties derived from a fragrance in a heating tool containing the fragrance, by using an exothermic composition containing an oxidation accelerator having an iodine adsorption of not higher than 500 mg/g, an oxidizable metal powder, and water.
Item 17. The method according to item 16, wherein the fragrance, the heating tool, and/or the exothermic composition have/has the feature according to any one of items 1 to 11.

Advantageous Effects of Invention

According to the heating tool of the present invention, by using an oxidation accelerator having an iodine adsorption of not higher than 500 mg/g, even when used after long-term storage, excellent aromatic properties can be sufficiently obtained, and exothermic effects sufficient for a heating tool can be obtained.

According to the heating tool of the present invention, excellent aromatic properties can be obtained upon usage even when the heating tool is stored in a state where the fragrance for perfuming the heating tool and the exothermic composition are in contact. Accordingly, in the heating tool of the present invention, the fragrance and the exothermic composition can exist in contact with each other, or can exist not in contact with each other.

According to the heating tool of the present invention, the types of fragrances are not limited, and therefore desired fragrances can be widely used.

BRIEF DESCRIPTION OF DRAWINGS

In FIG. 2, the fragrance is present in an adhesive component.

DESCRIPTION OF EMBODIMENTS

Figure 1:
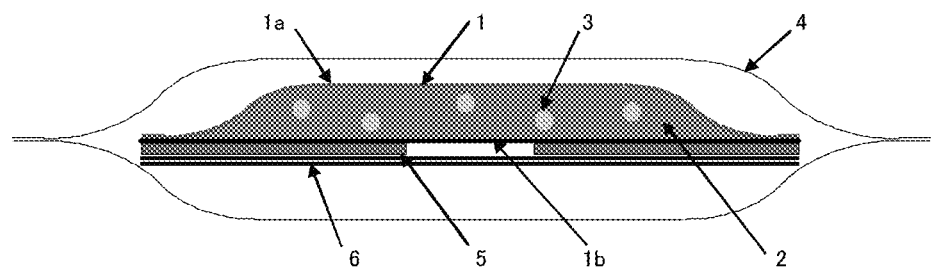
FIG. 1 shows an example of a stick-on type heating tool packaged in an outer bag. An air-permeable container bag illustrated in FIG. 1 is a model drawing of a container bag whose one side is an air-permeable portion and whose other side is an air-impermeable portion.

A heating tool of the present invention comprises an exothermic composition containing an oxidation accelerator having an iodine adsorption of not higher than 500 mg/g, an oxidizable metal powder, and water, and a fragrance, wherein at least the exothermic composition is housed in a container bag having air permeability. The heating tool of the present invention will be described below.

Exothermic Composition

The heating tool of the present invention contains an exothermic composition. The exothermic composition generates heat in the presence of oxygen, and contains an oxidation accelerator having an iodine adsorption of not higher than 500 mg/g, an oxidizable metal powder, and water.

Herein, any oxidation accelerator having an iodine adsorption of not higher than 500 mg/g may be employed. This is used for the purpose of promoting the supply of oxygen to the exothermic composition, especially to the oxidizable metal powder, by drawing in air. The oxidation accelerator has, for example, preferably an iodine adsorption of not higher than 400 mg/g, more preferably an iodine adsorption of not higher than 350 mg/g, further preferably an iodine adsorption of not higher than 300 mg/g, especially preferably an iodine adsorption of not higher than 250 mg/g, especially further preferably an iodine adsorption of not higher than 200 mg/g. The lower limit of the iodine adsorption is not particularly limited, but is theoretically 0 mg/g, for example.

Examples of the oxidation accelerator include, but not limited thereto as long as the-above mentioned conditions are met and desired effects are obtained, carbon black, graphite, activated carbon, coal, charcoal, bamboo charcoal, acetylene black, and waste coffee grounds charcoal. The oxidation accelerator is preferably carbon black, activated carbon, or charcoal, and more preferably carbon black. These may be used singly or in combination of two or more kinds. When two or more kinds are used in combination, the iodine adsorption of the combination (e.g., mixture) preferably satisfies the above-mentioned values. The iodine adsorption of the respective components can be easily known by a person of skill in the art, and the iodine adsorption is measured and calculated by the method defined in JIS K1474.

The heating tool of the present invention may be any heating tool as long as it generates heat so that a preferable temperature is attained upon usage, and an example of such a temperature is about 32 to 85° C., and is more preferably about 40 to 70° C. (measurement value based on JIS S4100 (2007)). From a perspective of generating heat to a more preferable temperature further efficiently, the oxidation accelerator preferably has electrical conductivity. The presence or absence of the electrical conductivity is known, and examples of known oxidation accelerators having electrical conductivity equal to or higher than a certain level include, but it is not limited to, carbon black, graphite, activated carbon, and the like.

In the present invention, the heat generation temperature of the heating tool is measured according to JIS S4100 (2007). More specifically, predetermined underlay material and covering material are laid on a warming portion defined in JIS S4100 (2007). The warming portion is heated to 30° C., and held within one degree of that temperature. Meanwhile, the heating tool left for 2 or more hours in an atmosphere having the same temperature as the ambient temperature is caused to generate heat based on the method of use. In accordance with a predetermined method, measurement is performed by measuring the time etc., required from the start of heat generation to returning to a predetermined temperature after exceeding the predetermined temperature and reaching the maximum temperature.

Although not limited as long as the desired effects are obtained, for example, from the standpoint of comfort when the heating tool is attached to the body, oxygen supply efficiency, etc., the oxidation accelerator is preferably in a form such as powdery, granular, and fibrous. These may be used singly or in combination of two or more kinds, and the average particle diameter of the oxidation accelerator is, for example, 0.001 to 1000 µm, preferably 0.005 to 500 µm, and more preferably 0.01 to 200 µm.

The amount of the oxidation accelerator is not limited as long as the desired effects are obtained. The proportion of the oxidation accelerator in the exothermic composition is, for example, 1 to 30 wt %, preferably 3 to 25 wt %, and more preferably 5 to 23 wt %.

The amount of the oxidation accelerator relative to the oxidizable metal powder described later is also not limited as long as the desired effects are obtained. The amount of the oxidation accelerator per 100 parts by weight of the oxidizable metal powder is, for example, 2 to 60 parts by weight, preferably 5 to 50 parts by weight, and more preferably 10 to 40 parts by weight.

The oxidizable metal powder contained in the exothermic composition is not limited as long as it is a metallic powder which generates heat when being oxidized. Examples thereof include iron powder, zinc powder, aluminum powder, magnesium powder, and copper powder. A preferable example is iron powder. Examples of the iron powder include reduced iron powder, cast-iron powder, atomized iron powder, and electrolytic-iron powder. These may be used singly or in combination of two or more kinds.

The oxidizable metal powder may be powdery, granular, or fibrous, and these may be used singly or in combination of two or more kinds.

Although not limited as long as the desired effects are obtained, from the standpoint of comfort when the heating tool is attached to the body, heat generation efficiency, etc., an example of the average particle diameter of oxidizable metal powder is 0.01 to 1000 µm, preferably 0.1 to 500 µm, and more preferably 0.5 to 300 µm. The average particle diameter of oxidizable metal powder can be measured by a JIS method using a standard sieve and the like.

The amount of the oxidizable metal powder is not limited as long as the desired effects are obtained. The proportion of the oxidizable metal powder in the exothermic composition is, for example, 20 to 80 wt %, preferably 40 to 70 wt %, and more preferably 45 to 60 wt %.

Usable water includes distilled water, tap water, ion exchange water, pure water, ultrapure water, industrial water, and the like.

The amount of water is also not limited as long as the desired effects are obtained. The proportion of water in the exothermic composition is, for example, 5 to 50 wt %, preferably 10 to 40 wt %, and more preferably 15 to 35 wt %.

In addition to the above-mentioned components, at least one substance selected from the group consisting of water soluble salts and water-retaining agents may be further blended in the exothermic composition if necessary.

The water soluble salt contained in the exothermic composition is blended in order to promote the oxidation of the oxidizable metal powder, and is not limited as long as the desired effects are obtained. Preferable examples of the water soluble salt include hydrochlorides and sulfates of alkali metals such as sodium and potassium; hydrochlorides and sulfates of alkaline earth metals such as calcium and magnesium; and hydrochlorides and sulfates of metals such as iron, copper, aluminum, zinc, nickel, silver, and barium. More preferable examples thereof include potassium chloride, sodium chloride, and the like. These may be used singly or in combination of two or more kinds. The blending of water soluble salt allows the heating tool to generate heat at a higher temperature, and maintain the temperature for a longer period of time. In particular, water soluble salt can be used for the purpose of causing the heating tool to generate heat at a higher temperature.

The amount of water soluble salt is also not limited as long as the desired effects are obtained. The proportion of the water soluble salt in the exothermic composition is, for example, 0.1 to 10 wt %, preferably 0.5 to 7 wt %, and more preferably 1 to 5 wt %.

The water-retaining agent has a function of retaining water, and is not limited as long as it has the function and can produce desired effects. Examples thereof include porous substances, water absorbing resins, and the like. Examples of the water-retaining agent include natural and synthetic inorganic substances such as vermiculite, perlite, calcium silicate, kaolin, talc, smectite, mica, bentonite, calcium carbonate, silica gel, alumina, zeolite, silicon dioxide, and diatomaceous earth; and natural and synthetic organic substances such as pulp, wood flour (sawdust), cotton, polyacrylate-based resins, polysulfonate-based resins, maleic anhydride salt-based resins, polyacrylamide-based resins, polyvinyl alcohol-based resins, polyethylene oxide-based resins, polyaspartate-based resins, polyglutamate-based resins, poly alginate-based resins, starches, and cellulose. Preferable examples thereof include vermiculite, wood flour, pulp, and polyacrylate-based resins. More preferable examples thereof include vermiculite and polyacrylate-based resins. These may be used singly or in combination of two or more kinds. The blending of the water-retaining agent allows the heating tool to generate heat at a higher temperature, and to maintain the temperature for a longer period of time. In particular, the water-retaining agent can be used for the purpose of sustaining the heat generation temperature in the heating tool for a longer period of time.

Although not limited as long as the desired effects are obtained, an example of the average particle diameter of the water-retaining agent is 0.1 to 3000 μm, preferably 0.5 to 1000 μm, and more preferably 1 to 500 μm. The average particle diameter of the water-retaining agent is also measured in a manner similar to the aforementioned method for measuring that of the oxidizable metal powder.

The amount of the water-retaining agent is also not limited as long as the desired effects are obtained. The proportion of the water-retaining agent in the exothermic composition is, for example, 1 to 20 wt %, preferably 3 to 15 wt %, and more preferably 5 to 10 wt %.

In these water-retaining agents, water-retaining agents having a porous structure, especially vermiculite etc., can serve not only as a water-retaining agent but also as an air passageway.

In addition to the above-mentioned components, other components which can be blended in the exothermic composition may be further blended in the exothermic composition if necessary. Examples of such a component include, but are not limited to, surfactants, hydrogen generation inhibitors, thickening agents, and excipients.

In a hitherto known heating tool, activated carbon having an iodine adsorption greater than 500 mg/g has been widely used as a component of the exothermic composition to promote oxidation. In the heating tool of the present invention, containing activated carbon which has been hitherto used is not excluded as long as the desired effects are obtained. Preferably, from the standpoint of further suppressing or preventing the loss or alteration of the aromatic properties of the heating tool during storage, when activated carbon having high adsorptive capability which has been hitherto used is contained in the exothermic composition used for the heating tool of the present invention, the amount of the activated carbon is set to be small enough that the aromatic properties are not lost or altered during storage, or activated carbon having high adsorptive capability is not contained. More preferably, from a similar perspective, in the heating tool of the present invention, the amount of activated carbon having high adsorptive capability which has been hitherto used is set to be small so that the aromatic properties are not lost or altered during storage, or activated carbon is not contained.

In the exothermic composition, the total amount of the oxidation accelerator having an iodine adsorption of not higher than 500 mg/g, the oxidizable metal powder, and water is not limited as long as the desired effects are obtained, and the heat generation temperature in the exothermic composition may be suitably set to be a temperature (e.g., about 32 to 85° C., measurement value according to JIS S4100) preferable for the heating tool.

As an embodiment of the exothermic composition used for the heating tool of the present invention, the amounts of the components in the exothermic composition are, for example, as follows: 1 to 40 wt % for the oxidation accelerator, 20 to 80 wt % for the oxidizable metal powder, and 5 to 50 wt % for water.

As another embodiment of the exothermic composition used for the heating tool of the present invention, the amounts of the components in the exothermic composition are, for example, as follows: 1 to 30 wt % for the oxidation accelerator, 20 to 80 wt % for the oxidizable metal powder, 0.1 to 10 wt % for the water soluble salt, and 5 to 50 wt % for water.

As another embodiment of the exothermic composition used for the heating tool of the present invention, the amounts of the components in the exothermic composition are, for example, as follows: 1 to 30 wt % for the oxidation accelerator, 20 to 80 wt % for the oxidizable metal powder, 1 to 20 wt % for the water-retaining agent, and 5 to 50 wt % for water.

As another embodiment of the exothermic composition used for the heating tool of the present invention, the amounts of the components in the exothermic composition are, for example, as follows: 1 to 30 wt % for the oxidation accelerator, 20 to 80 wt % for the oxidizable metal powder, 0.1 to 10 wt % for the water soluble salt, 1 to 20 wt % for the water-retaining agent, and 5 to 50 wt % for water. The amounts of the components in the exothermic composition are, for example, as follows: 5 to 35 wt % for the oxidation accelerator, 45 to 60 wt % for the oxidizable metal powder, 1 to 5 wt % for the water soluble salt, 5 to 10 wt % for the water-retaining agent, and 15 to 35 wt % for water.

In an embodiment of the exothermic composition used for the heating tool of the present invention, the composition contains, for example, carbon black having an iodine adsorption of not higher than 500 mg/g, iron powder, and water. In another embodiment of the exothermic composition used for the heating tool of the present invention, the composition contains, for example, carbon black having an iodine adsorption of not higher than 500 mg/g, iron powder, sodium chloride, and water. In another embodiment of the exothermic composition used for the heating tool of the present invention, the composition contains, for example, carbon black having an iodine adsorption of not higher than 500 mg/g, iron powder, a water-absorbing resin and/or vermiculite, and water. In another embodiment of the exothermic composition used for the heating tool of the present invention, the composition contains, for example, carbon black having an iodine adsorption of not higher than 500 mg/g, iron powder, sodium chloride, a water-absorbing resin and/or vermiculite, and water.

In the embodiments described above, the oxidation accelerator that is used preferably has an iodine adsorption of 0 to 400 mg/g, more preferably has an iodine adsorption of 0 to 350 mg/g, further preferably has an iodine adsorption of 0 to 300 mg/g, especially preferably has an iodine adsorption of 0 to 250 mg/g, and especially further preferably has an iodine adsorption of 0 to 200 mg/g. In these embodiments, the oxidation accelerator more preferably has electrical conductivity.

The exothermic composition is prepared by mixing the above components. The exothermic composition may be prepared in the presence of oxygen or may be prepared in vacuum or in an inert gas atmosphere. These can be prepared according to a hitherto known procedure.

In the heating tool of the present invention, as described above, the oxidation accelerator having an iodine adsorption of not higher than 500 mg/g is used. Therefore, by preparing the exothermic composition according to the aforementioned description, loss or alteration of the aromatic properties of the heating tool during storage can be suppressed or prevented. Therefore, even after being stored for a long period of time, excellent aromatic properties can be obtained upon usage, and heat keeping effects sufficient for a heating tool can be obtained.

As used herein, the term "comprise", in addition to its standard meaning, also includes the meaning of "consist essentially of" and the meaning of "consist of".

Air-Permeable Container Bag for Housing Exothermic Composition

In the heating tool of the present invention, the exothermic composition is housed in an air-permeable container bag for housing the exothermic composition (hereinafter, sometimes described as "container bag for the exothermic composition"). The air-permeable container bag for housing the exothermic composition is capable of housing the exothermic composition and is not limited as long as it has air-permeability, and a hitherto known container bag can be used. For example, as the container bag for the exothermic composition, from the standpoints of preventing leakage of the exothermic composition, having durability against the heat generation by the exothermic composition, and improving the ease of use of the heating tool etc., for example, an air-permeable bag and the like used in hitherto known disposable hand warmers can be used.

In a non-limiting more specific example, the container bag for the exothermic composition has a laminated structure in which an air-permeable resin film is laminated on an air-permeable woven fabric or nonwoven fabric. In this case, the air-permeable resin film is arranged on the inside of the container bag for the exothermic composition, and the air-permeable woven fabric or nonwoven fabric is arranged on the outside of the container bag for the exothermic composition.

The resin used for the air-permeable resin film is not particularly limited, but preferable examples thereof include thermoplastic resins. Examples of the thermoplastic resins include polyethylene, polypropylene, polyester, polyamide, polyurethane, polystyrene, polyvinyl alcohol, polyvinyl chloride, polyvinylidene chloride, polycarbonate, ethylene-vinyl acetate copolymers, and the like. From the standpoint of usage of the heating tool as being attached to the body, preferable examples of the thermoplastic resin include polyethylene, polypropylene, ethylene-vinyl acetate copolymers, and the like. These may be used singly or in combination of two or more kinds.

In the air-permeable resin film used in the present invention, pores for ensuring the air permeability in the resin film formed by the resin are provided at least partially. The pores allow air to move in and out of the container bag for the exothermic composition, and are not limited as long as they are of sufficient size to prevent leakage of the exothermic composition to the outside of the container bag. When, for example, the heating tool is used by being attached to the body, the sensible temperature of the heating tool upon usage can be affected by the air permeability of the container bag for the exothermic composition, and therefore the size, shape, and number of the pores may be suitably determined considering the sensible temperature of the heating tool upon usage. Means for forming pores in the resin film are hitherto known, and a known procedure can be followed.

Examples of the fiber materials of the air-permeable woven fabric or nonwoven fabric include synthetic fibers such as nylon, vinylon, polyester, rayon, acrylic, polyethylene, polypropylene, acetate, polyvinyl chloride, and polybutylene terephthalate, natural fibers such as cotton, hemp, silk, and paper, mixed fibers of synthetic fibers and natural fibers, and the like. From the perspective of sense of use, examples of the fiber materials include nylon, polyester, polypropylene, and the like, and more preferably nylon and polyester. These may be used singly or in combination of two or more kinds. The woven fabric or nonwoven fabric is not limited as long as the fabric allows air to move in and out of the container bag for the exothermic composition, and can prevent leakage of the exothermic composition to the outside of the container bag. The weight per area of the fabric is, for example, preferably 25 to 70 $g/m^2$.

The laminate of the air-permeable resin film and air-permeable woven fabric or nonwoven fabric is not limited as long as the obtained laminate is strong enough as the container bag for the exothermic composition and ensures air permeability. The laminate can be formed by, for example, a lamination method, and examples of the lamination method include methods of laminating by thermal bond, and methods of laminating using an adhesive such as hot-melt adhesives, acrylic adhesives, or urethane adhesives. These laminates may be formed partially or entirely on the surface of the container bag for the exothermic composition as long as the desired effects are obtained.

Commercially available products may be used as the container bag for the exothermic composition.

The size and shape of the container bag for the exothermic composition are also not limited as long as the desired effects are obtained, and may be suitably determined depending on the purpose of use.

For example, when the heating tool of the present invention is attached to clothing, skin, or the like to be used, an adhesive sheet for fixing the heating tool of the present invention on the clothing, skin, or the like with a peelable force can be provided on the outside of the container bag for the exothermic composition. Examples of such an adhesive sheet include hitherto known adhesive sheets used for so-called stick-on type disposable hand warmer for application on clothing etc., and hitherto known skin-direct stick-on type adhesive sheets to be directly attached to the skin etc. Additionally, an optional adhesive component, if necessary, may be provided on the outside of the container bag for the exothermic composition used for the heating tool of the present invention.

Fragrance

The heating tool of the present invention contains a fragrance. The fragrance may be suitably determined depending on the use and preference and is not limited. Natural fragrances such as essential oils can be used singly or in combination, or synthetic fragrances can be used singly or in combination. Natural fragrances and synthetic fragrances can also be freely combined to be used as a compound fragrance. Examples of the natural fragrances (essential oils) include, but are not limited to, vanilla, lavender, chamomile, rosemary, sage, citronella, ginger, ylang-ylang, eucalyptus, mint, rose, lily, lilac, jasmine, cardamom, lemon grass, yuzu, orange, lemon, lime, grapefruit, neroli, cedar wood, sandalwood, anise, caraway, amber, musk, civet, castoreum, and the like. Examples of the synthetic fragrances include, but are not limited to, acetophenone, aldehyde $C_6$-$C_{16}$, allyl caproate, amylcinnamic aldehyde, amyl salicylate, benzaldehyde, benzyl acetate, benzyl alcohol, borneol, camphor, cinnamic alcohol, citral, citronellal, citronellol, coumarin, damascone, dehydrolinalool, dihydromyrcenol, diphenyl oxide, ethyl-2-methyl butyrate, ethyl butyrate, eugenol, geraniol, geranyl acetate, phenylethyl alcohol, hedione, hexanol, cis-3-hexanol, α-hexyl cinnamic aldehyde, isoamyl acetate, lilial, limonene, linalool, linalyl acetate, 1-menthol, methyl benzoate, methyl ionone, methyl salicylate, nerol, α-pinene, β-pinene, rose oxide, terpineol, γ-nonalactone, γ-undecalactone, vanillin, and the like. Since aromatic properties can be enhanced by the heat generated in the heating tool, as the fragrance, a fragrance that can vaporize at a temperature (e.g., about 32 to 85° C.) at which the exothermic composition generates heat in the presence of air is more preferable. The fragrance may be liquid, solid, or the like.

The amount of the fragrance in the heating tool of the present invention is not limited as long as the desired effects are obtained. The amount of the fragrance is, for example, 0.0001 to 5 parts by weight, preferably 0.01 to 1 parts by weight, and more preferably 0.05 to 0.6 parts by weight, per 100 parts by weight of the exothermic composition.

The amount of the fragrance, per 100 parts by weight of the oxidation accelerator having an iodine adsorption of not higher than 500 mg/g in the exothermic composition, is, for example, 0.0003 to 500 parts by weight, preferably 0.003 to 100 parts by weight, more preferably 0.01 to 50 parts by weight, and further preferably 0.17 to 50 parts by weight.

The amount of the fragrance, per 100 parts by weight of the oxidizable metal powder in the exothermic composition, is, for example, 0.0001 to 25 parts by weight, preferably 0.01 to 5 parts by weight, and more preferably 0.05 to 2.5 parts by weight.

The way the fragrance is included in the heating tool of the present invention is not limited as long as aroma can be imparted to the heating tool, and the fragrance may be further housed in the air-permeable container bag, or may exist outside the container bag.

More specifically, regarding the way the fragrance is included in the heating tool of the present invention, for example, the fragrance may be mixed with the components of the exothermic composition and housed in the container bag; the fragrance may be contained in at least a portion of the container bag for the exothermic composition; or the fragrance may be contained in advance in another sheet or in an optional adhesive component, etc. or housed in another air-permeable container bag or the like, and the sheet, the adhesive component, or the container bag etc., may be disposed inside, outside of, and/or on the outside of the container bag for the exothermic composition.

When the fragrance is mixed with the components in the exothermic composition, for example: the fragrance itself may be mixed with the components; a mixture obtained by mixing water etc., with the fragrance by using a surfactant or the like may be mixed with the components; the fragrance or the mixture may be encapsulated in advance in hitherto known microcapsules, and the obtained encapsulated microcapsules may be mixed with the components; or the fragrance or the mixture may be supported on a carrier and then mixed with the components. From the standpoint of preventing adhesion of the fragrance to the components in the exothermic composition as much as possible, in particular, from the standpoint of preventing adhesion of the fragrance to the oxidation accelerator and the oxidizable metal powder as much as possible, for example, the fragrance is preferably supported on a carrier in advance, and then mixed with the components. Examples of the carrier include, but not limited to unless the effects of the present invention are hindered, silica, vermiculite, perlite, fluorite, zeolite, fine silicon dioxide, pulp, plastics, rubbers, and elastomers. The particle diameter of the carrier is also not limited unless the effects of the present invention are hindered. An example of the average particle diameter is about 0.1 to 3000 μm, preferably about 0.5 to 1000 μm, more preferably about 1 to 500 μm. The amount of the carrier is also not limited unless the effects of the present invention are hindered.

When supporting the fragrance, for example, the fragrance may be supported on the components contained in the exothermic composition. From the standpoint of the influence on heat generation, the fragrance is preferably supported on components other than the oxidation accelerator and oxidizable metal powder in the exothermic composition. For example, when the exothermic composition contains a water-retaining agent, the fragrance may be preferably supported on the water-retaining agent contained in the exothermic composition.

As described above, when the fragrance is contained in at least a portion of the container bag for the exothermic composition, for example, the container bag may be impregnated with the fragrance in advance, or the fragrance may be kneaded into at least one of the film, the woven fabric, and the nonwoven fabric constituting the container bag in advance. As another example, when the fragrance is contained in at least a portion of the container bag for the exothermic composition, the fragrance may be encapsulated in microcapsules, and these may be deposited on at least one of the film, woven fabric and nonwoven fabric constituting the container bag.

As described above, in a case where the fragrance is contained in advance in another sheet or in an optional adhesive component etc. or housed in another air-permeable container bag etc., and the sheet, the adhesive component, or the container bag etc., is disposed inside, outside of, and/or on the outside of the container bag for the exothermic composition; examples of the sheet and the adhesive component etc., include hitherto known adhesive sheets used for so-called stick-on type disposable hand warmers, skin-direct stick-on type adhesive sheets, and adhesive components etc., used therefor. The air-permeable container bag in which the fragrance is housed in advance is, for example, a container bag similar to the aforementioned container bag for the exothermic composition.

Accordingly, in the heating tool of the present invention, since the oxidation accelerator having an iodine adsorption of not higher than 500 mg/g is contained in the exothermic composition, the adsorption of the fragrance by the oxidation accelerator can be suppressed or prevented. Thus, even when the fragrance and the exothermic composition exist in contact with each other in the heating tool of the present invention, loss or alteration of the aromatic properties during storage can be suppressed or prevented as long as the heating tool is stored in an environment preventing contact with oxygen. Therefore, in the heating tool of the present invention, it is not essential to dispose the fragrance and the exothermic composition so that they do not come into contact with each other.

Furthermore, when the fragrance contained in the heating tool of the present invention is a fragrance having a relaxing effect, such as lavender or chamomile, the heating tool of the present invention is considered to further have a relaxing effect. When the fragrance contained in the heating tool of the present invention is a fragrance having an insect-repelling effect, such as eucalyptus oil, the heating tool of the present invention is considered to further have an insect-repelling effect. Accordingly, the heating tool of the present invention is considered to have additional effects (functions) depending on the characteristics of the fragrance to be used. The effects (functions) of the fragrances are hitherto known.

The heating tool of the present invention may contain optional components in addition to the fragrance. Examples of such components include insect-repelling components such as pyrethroid and paramenthane, other relaxing components including warm sensation components such as capsicum extract and nonylic acid vanillyl amide, and cool sensation components such as the aforementioned 1-menthol and camphor. Such optional components can be contained within a range that does not hinder the effects of the present invention. The amounts of these components may be suitably set within a range that does not hinder the effects of the present invention.

Heating Tool

The heating tool of the present invention comprises the exothermic composition and the fragrance, wherein at least the exothermic composition is housed in a container bag having air permeability. The heating tool of the present invention is produced by housing the exothermic composition prepared as described above in the aforementioned air-permeable container bag, including the fragrance as described above, and, if necessary, suitably including the optional components.

The thus-produced heating tool, in general, is further packaged in the air-impermeable outer bag preventing permeation of oxygen to be provided or stored while maintaining an airtight state. In the heating tool of the present invention, since the exothermic composition generates heat upon contact with oxygen, it is important to prevent the heating tool from contacting oxygen during storage to prevent heat generation until usage. Upon usage, the heating tool of the present invention may be used by opening the outer bag, taking the heating tool out from the outer bag, and bringing the exothermic composition into contact with oxygen to generate heat. The outer bag used herein is not particularly limited as long as it is an air-impermeable bag which does not allow permeation of oxygen.

Such a heating tool can be used for the purpose of warm-keeping, blood circulation promotion, fatigue alleviation, relaxation, etc. Therefore, it can be used as aesthetic and medical devices, including warming tool such as perfumed disposable hand warmer and perfumed face packs, blood circulation improving tools, fatigue alleviating tools, and warming treatment tools. For example, it can be applied to desired body parts, such as eyes, neck, shoulders, elbows, back, waist, knees, and legs. The heating tool of the present invention can be also used as a fragrance tool, an insect repellent tool, and an insecticide, etc. The targets of application of the heating tool of the present invention are not limited to the body parts mentioned above, and can be also used for the purpose of warm-keeping of objects other than the body such as food, slowing the cooling rate of the objects, etc. The heating tool of the present invention, further has additional values depending on the effects (functions) provided by the fragrance and the effects (functions) provided by the optional components as described above.

Accordingly, in the heating tool of the present invention, particularly in the exothermic composition, an oxidation accelerator having an iodine adsorption of not higher than 500 mg/g is contained, and therefore the adsorption of the fragrance by the oxidation accelerator is suppressed or prevented. Thus, the loss or alteration of the aromatic properties during storage can be suppressed or prevented as long as the heating tool is stored in an environment preventing contact with oxygen, and therefore, even after being stored for a long period of time, excellent aromatic properties can be obtained upon usage, and further heat keeping effects sufficient for a heating tool can be obtained.

According to the heating tool of the present invention, even when the fragrance for perfuming the heating tool and the exothermic composition are in contact while the heating tool is stored for a long period of time, excellent aromatic properties can be obtained upon usage. Accordingly, in the heating tool of the present invention, the fragrance and the exothermic composition can exist in a state of being in contact with each other, or can exist in a state of not being in contact. In the heating tool of the present invention, when the fragrance is disposed outside of or on the outside of the container bag for the exothermic composition without being in direct contact with the exothermic composition, and it is packaged and stored in the air-impermeable outer bag, aroma may fill the space in the outer bag in some cases. Even in such a case, according to the heating tool of the present invention, the adsorption of the filled fragrance (aroma) by the oxidation accelerator in the exothermic composition can be suppressed or prevented. Therefore, according to the present invention, a heating tool having various configurations not limited by the arrangement relationship between the fragrance and the exothermic composition can be obtained.

According to such a heating tool of the present invention, since the types of fragrances are not limited, desired fragrances can be widely used.

By using the oxidation accelerator that has electrical conductivity equal to or higher than a certain level, in the heating tool of the present invention, the exothermic effects as the heating tool can be obtained more efficiently. When the water soluble salt and/or water-retaining agent are/is blended in the heating tool of the present invention, the heating tool can be caused to generate heat at a higher temperature, and the temperature can be sustained for a longer period of time. The water soluble salt can be used particularly for the purpose of generating heat at a higher temperature, and the water-retaining agent can be used particularly for the purpose of sustaining the heat generation temperature in the heating tool for a longer period of time. When the water soluble salt and water-retaining agent are used in combination, heat can be generated at a higher temperature, and the temperature can be sustained for a longer period of time.

Accordingly, the present invention provides, for producing the heating tool containing the fragrance, the use of the exothermic composition which contains the oxidation accelerator having an iodine adsorption of not higher than 500 mg/g, the oxidizable metal powder, and water. The present invention, in order to sustain the aromatic properties derived from the fragrance in the heating tool containing the fragrance, provides the use of the exothermic composition which contains an oxidation accelerator having an iodine adsorption of not higher than 500 mg/g, the oxidizable metal powder, and water. The present invention provides a method for sustaining the aromatic properties derived from the fragrance in a heating tool containing the fragrance by using the exothermic composition which contains the oxidation accelerator having an iodine adsorption of not higher than 500 mg/g, the oxidizable metal powder, and water. In these, the heating tool, the exothermic composition, the components included therein such as the oxidation accelerator having an iodine adsorption of not higher than 500 mg/g, the oxidizable metal powder, water, and the fragrance, their amounts, their production methods, application methods, and other conditions are as described above.

EXAMPLES

The present invention will be described below by means of Examples, but the present invention is not limited to Examples provided below.

Example 1

Heating tools having the structure shown in FIG. 1 (heating tools 1-1 to 1-3) were produced by the procedure described below, and the aroma intensities and heat keeping effects of the heating tools after being stored were evaluated. A comparative heating tool 1 described below was produced as a Comparative Example, and the aroma intensity and heat keeping effects after storage were evaluated by a similar method.

(1) Production of Heating Tool

Production of Heating Tool 1-1

A heating tool was produced by the procedure described below.

The components described below were used in an exothermic composition.

<Exothermic Composition>
Iron powder (manufactured by DOWA IP Creation Co., Ltd., product name: DKP, average particle diameter: 100 μm)
Carbon black (manufactured by Mitsubishi Chemical Corp., product name: RCF, iodine adsorption: 144 mg/g, average particle diameter: 0.075 μm, electrically conductive)
Water
Vermiculite (average particle diameter: about 500 μm)
Water-absorbing resin (acrylic acid polymer partial salt crosslinked product, average particle diameter: 250 μm)
Common salt The fragrance described below was used as a fragrance.
<Fragrance>
Chamomile (fragrance number: BR11880, manufactured by Ogawa & Co., Ltd.)

The components of the exothermic composition and the fragrance were mixed to obtain a mixture. Herein, the proportions of the iron powder, the carbon black, the water, the vermiculite, the water-absorbing resin, the common salt, and the fragrance were 50 wt %, 20 wt %, 20 wt %, 5 wt %, 2.5 wt %, 2 wt %, and 0.5 wt %, respectively. The obtained mixture was housed and sealed in an air-permeable container bag (130×95 mm) (1 in FIG. 2) made of a porous film (manufactured by Nitto Lifetech Corp., product name: Breathron) to which an air-impermeable adhesive sheet (manufactured by Nitto Lifetech Corp., product name: Nitotac) (5 and 6 in FIG. 2) was partially attached, giving a heating tool 1-1. The heating tool 1-1 was then quickly packaged in an air-impermeable outer bag for a disposable hand warmer.

Production of Heating Tool 1-2

A heating tool was produced by the procedure described below.

The components described below were used in an exothermic composition.

<Exothermic Composition>
Iron powder (manufactured by DOWA IP Creation Co., Ltd., product name: DKP, average particle diameter: 100 μm)
Carbon black (manufactured by Mitsubishi Chemical Corp., product name: HCF, iodine adsorption: 308 mg/g, average particle diameter: 0.016 electrically conductive)
Water
Vermiculite (average particle diameter: about 500 μm)
Water-absorbing resin (acrylic acid polymer partial salt crosslinked product, average particle diameter: 250 μm)
Common salt The fragrance described below was used as a fragrance.
<Fragrance>
Chamomile (fragrance number: BR11880, manufactured by Ogawa & Co., Ltd.)

The components of the exothermic composition and the fragrance were mixed to obtain a mixture. Herein, the proportions of the iron powder, the carbon black, the water, the vermiculite, the water-absorbing resin, the common salt, and the fragrance were 50 wt %, 20 wt %, 20 wt %, 5 wt %, 2.5 wt %, 2 wt %, and 0.5 wt %, respectively. The obtained mixture was housed and sealed in an air-permeable container bag (130×95 mm) made of a porous film (manufactured by Nitto Lifetech Corp., product name: Breathron) to which an air-impermeable adhesive sheet (manufactured by Nitto Lifetech Corp., product name: Nitotac) was partially attached, giving a heating tool 1-2. The heating tool 1-2 was then quickly packaged in an air-impermeable outer bag for a disposable hand warmer.

Production of Heating Tool 1-3

A heating tool was produced by the procedure described below.

The components described below were used in an exothermic composition.

<Exothermic Composition>
Iron powder (manufactured by DOWA IP Creation Co., Ltd., product name: DKP, average particle diameter: 100 μm)
Carbon black (manufactured by Mitsubishi Chemical Corp., product name: HCF, iodine adsorption: 400 mg/g, average particle diameter: 0.013 electrically conductive)
Water
Vermiculite (average particle diameter: 500 μm)
Water-absorbing resin (acrylic acid polymer partial salt crosslinked product, average particle diameter: 250 μm)
Common salt The fragrance described below was used as a fragrance.
<Fragrance>
Chamomile (fragrance number: BR11880, manufactured by Ogawa & Co., Ltd.)

The components of the exothermic composition and the fragrance were mixed to obtain a mixture. Herein, the proportions of the iron powder, the carbon black, the water, the vermiculite, the water-absorbing resin, the common salt, and the fragrance were 50 wt %, 20 wt %, 20 wt %, 5 wt %, 2.5 wt %, 2 wt %, and 0.5 wt %, respectively. The obtained mixture was housed and sealed in an air-permeable container bag (130×95 mm) made of a porous film (manufactured by Nitto Lifetech Corp., product name: Breathron) to which an air-impermeable adhesive sheet (manufactured by Nitto Lifetech Corp., product name: Nitotac) was partially attached, giving a heating tool 1-3. The heating tool 1-3 was then quickly packaged in an air-impermeable outer bag for a disposable hand warmer.

Production of Comparative Heating Tool 1

A heating tool was produced by the procedure described below.

The components described below were used in an exothermic composition.

<Exothermic Composition>
Iron powder (manufactured by DOWA IP Creation Co., Ltd., product name: DKP, average particle diameter: 100 μm)
Activated carbon (Futamura Chemical Co., Ltd., product name: Taiko Kasseitan, iodine adsorption: 1050 mg/g, average particle diameter: 50 μm, electrically conductive)
Water
Vermiculite (average particle diameter: 500 μm)

Water-absorbing resin (acrylic acid polymer partial salt crosslinked product, average particle diameter: 250 μm)

Common salt

The fragrance described below was used as a fragrance.

<Fragrance>

Chamomile (fragrance number: BR11880, manufactured by Ogawa & Co., Ltd.)

The components of the exothermic composition and the fragrance were mixed to obtain a mixture. Herein, the proportions of the iron powder, the activated carbon, the water, the vermiculite, the water-absorbing resin, the common salt, and the fragrance were 50 wt %, 20 wt %, 20 wt %, 5 wt %, 2.5 wt %, 2 wt %, and 0.5 wt %, respectively. The obtained mixture was housed and sealed in an air-permeable container bag (130×95 mm) made of a porous film (manufactured by Nitto Lifetech Corp., product name: Breathron) to which an air-impermeable adhesive sheet (manufactured by Nitto Lifetech Corp., product name: Nitotac) was partially attached, giving a comparative heating tool 1. The comparative heating tool 1 was then quickly packaged in an air-impermeable outer bag for a disposable hand warmer.

(2) Storage of Heating Tool Produced

Each of the heating tools produced was stored in a thermostatic chamber at 50° C. in the presence of oxygen for 30 days. This storage condition corresponds to storage at room temperature (25° C.) for 1.5 years.

(3) Evaluation of Heating Tool after Storage

After storage, the outer bag was opened to remove the heating tool, and the intensity of aroma of each of the heating tools was evaluated. Specifically, five subjects were asked to smell the aroma of each of the heating tools removed from the outer bag, and evaluate the intensity of the aroma on a scale of 1 to 5 described below. The higher the value of the aroma intensity, the better the evaluation and the more intense the remaining aroma. Simultaneously, the subjects were also asked to evaluate whether heat was generated at a level sufficient for practical use in each of the heating tools.

<Evaluation of Intensity of Aroma>

1: Odorless
2: Slightly fragrant
3: Moderately fragrant
4: Strongly fragrant
5: Very strongly fragrant

TABLE 1

|  | Heating tool | Aroma | Subject 1 | Subject 2 | Subject 3 | Subject 4 | Subject 5 | Average |
|---|---|---|---|---|---|---|---|---|
| Aroma intensity evaluation | Heating tool 1-1 | Chamomile | 5 | 4 | 5 | 4 | 5 | 4.6 |
|  | Heating tool 1-2 |  | 3 | 3 | 3 | 2 | 3 | 2.8 |
|  | Heating tool 1-3 |  | 2 | 2 | 2 | 1 | 2 | 1.8 |
|  | Comparative heating tool 1 |  | 1 | 1 | 1 | 1 | 1 | 1.0 |

As can be clearly observed from the results shown in Table 1, the aroma component was adsorbed in the heating tool using activated carbon having a high iodine adsorption, rendering the heating tool odorless, while the aroma was left unadsorbed to the heating tools using carbon black with low iodine adsorption capacities. All of heating tools 1-1 to 1-3 were confirmed as able to generate heat at a level sufficient for practical use, and provide sufficient heat keeping effect.

Example 2

Heating tools having the structure shown in FIG. 1 (heating tool 2-1 and heating tool 2-2) were produced by the procedure described below, and the aroma intensities and heat keeping effects of the heating tools after being stored were evaluated. A comparative heating tool 2 described below was produced as a Comparative Example, and the aroma intensity and heat keeping effects after storage were evaluated by a similar method. The above-described comparative heating tool 1 was also evaluated as well.

(1) Production of Heating Tool

Production of Heating Tool 2-1

A heating tool was produced by the procedure described below.

The components described below were used in an exothermic composition.

<Exothermic Composition>

Iron powder (manufactured by DOWA IP Creation Co., Ltd., product name: DKP, average particle diameter: 100 μm)

Carbon black (manufactured by Mitsubishi Chemical Corp., product name: RCF, iodine adsorption: 144 mg/g, average particle diameter: 0.075 μm, electrically conductive)

Activated carbon (Futamura Chemical Co., Ltd., product name: Taiko Kasseitan, iodine adsorption: 1050 mg/g, average particle diameter: 50 μm, electrically conductive)

Water

Vermiculite (average particle diameter: 500 μm)

Water-absorbing resin (acrylic acid polymer partial salt crosslinked product, average particle diameter: 250 μm)

Common salt

The fragrance described below was used as a fragrance.

<Fragrance>

Chamomile (fragrance number: BR11880, manufactured by Ogawa & Co., Ltd.)

The components of the exothermic composition and the fragrance were mixed to obtain a mixture. Herein, the proportions of the iron powder, the carbon black, the activated carbon, the water, the vermiculite, the water-absorbing resin, the common salt, and the fragrance were 50 wt %, 18 wt %, 2 wt %, 20 wt %, 5 wt %, 2.5 wt %, 2 wt %, and 0.5 wt %, respectively. The obtained mixture was housed and sealed in an air-permeable container bag (130×95 mm) made of a porous film (manufactured by Nitto Lifetech Corp., product name: Breathron) to which an air-impermeable adhesive sheet (manufactured by Nitto Lifetech Corp., product name: Nitotac) was partially attached, giving a heating tool 2-1. The iodine adsorption of the oxidation accelerator in the heating tool 2-1 was about 240 mg/g. The heating tool 2-1 was then quickly packaged in an air-impermeable outer bag for a disposable hand warmer.

Production of Heating Tool 2-2

A heating tool was produced by the procedure described below.

The components described below were used in an exothermic composition.

<Exothermic Composition>
Iron powder (manufactured by DOWA IP Creation Co., Ltd., product name: DKP, average particle diameter: 100 μm)
Carbon black (manufactured by Mitsubishi Chemical Corp., product name: RCF, iodine adsorption: 144 mg/g, average particle diameter: 0.075 μm, electrically conductive)
Activated carbon (Futamura Chemical Co., Ltd., product name: Taiko Kasseitan, iodine adsorption: 1050 mg/g, average particle diameter: 50 μm, electrically conductive)
Water
Vermiculite (average particle diameter: 500 μm)
Water-absorbing resin (acrylic acid polymer partial salt crosslinked product, average particle diameter: 250 μm)
Common salt
The fragrance described below was used as a fragrance.
<Fragrance>
Chamomile (fragrance number: BR11880, manufactured by Ogawa & Co., Ltd.)

The components of the exothermic composition and the fragrance were mixed to obtain a mixture. Herein, the proportions of the iron powder, the carbon black, the activated carbon, the water, the vermiculite, the water-absorbing resin, the common salt, and the fragrance were 50 wt %, 15 wt %, 5 wt %, 20 wt %, 5 wt %, 2.5 wt %, 2 wt %, and 0.5 wt %, respectively. The obtained mixture was housed and sealed in an air-permeable container bag (130×95 mm) made of a porous film (manufactured by Nitto Lifetech Corp., product name: Breathron) to which an air-impermeable adhesive sheet (manufactured by Nitto Lifetech Corp., product name: Nitotac) was partially attached, giving a heating tool 2-2. The iodine adsorption of the oxidation accelerator in the heating tool 2-2 was about 370 mg/g. The heating tool 2-2 was then quickly packaged in an air-impermeable outer bag for a disposable hand warmer.

Production of Comparative Heating Tool 2
A heating tool was produced by the procedure described below.
The components described below were used in an exothermic composition.
<Exothermic Composition>
Iron powder (manufactured by DOWA IP Creation Co., Ltd., product name: DKP, average particle diameter: 100 μm)
Carbon black (manufactured by Mitsubishi Chemical Corp., product name: RCF, iodine adsorption: 144 mg/g, average particle diameter: 0.075 μm, electrically conductive)
Activated carbon (Futamura Chemical Co., Ltd., product name: Taiko Kasseitan, iodine adsorption: 1050 mg/g, average particle diameter: 50 μm, electrically conductive)
Water
Vermiculite (average particle diameter: 500 μm)
Water-absorbing resin (acrylic acid polymer partial salt crosslinked product, average particle diameter: 250 μm)
Common salt
The fragrance described below was used as a fragrance.
<Fragrance>
Chamomile (fragrance number: BR11880, manufactured by Ogawa & Co., Ltd.)

The components of the exothermic composition and the fragrance were mixed to obtain a mixture. Herein, the proportions of the iron powder, the carbon black, the activated carbon, the water, the vermiculite, the water-absorbing resin, the common salt, and the fragrance were 50 wt %, 10 wt %, 10 wt %, 20 wt %, 5 wt %, 2.5 wt %, 2 wt %, and 0.5 wt %, respectively. The obtained mixture was housed and sealed in an air-permeable container bag (130×95 mm) made of a porous film (manufactured by Nitto Lifetech Corp., product name: Breathron) to which an air-impermeable adhesive sheet (manufactured by Nitto Lifetech Corp., product name: Nitotac) was partially attached, giving a comparative heating tool 2. The iodine adsorption of the oxidation accelerator in the comparative heating tool 2 was about 600 mg/g. The comparative heating tool 2 was then quickly packaged in an air-impermeable outer bag for a disposable hand warmer.

(2) Storage of Heating Tool Produced
Each of the heating tools produced was stored in a thermostatic chamber at 50° C. in the presence of oxygen for 30 days. This storage condition corresponds to storage at room temperature (25° C.) for 1.5 years.

(3) Evaluation of Heating Tool after Storage
After storage, the outer bag was opened to remove the heating tool, and the intensity of aroma of each of the heating tools was evaluated. Specifically, five subjects were asked to smell the aroma of each of the heating tools removed from the outer bag, and evaluate the intensity of the aroma on a scale of 1 to 5 described below. The higher the value of the aroma intensity, the better the evaluation and the more intense the remaining aroma. Simultaneously, the subjects were also asked to evaluate whether heat was generated at a level sufficient for practical use in each of the heating tools.

<Evaluation of Intensity of Aroma>
1: Odorless
2: Slightly fragrant
3: Moderately fragrant
4: Strongly fragrant
5: Very strongly fragrant

TABLE 2

|  | Heating tool | Aroma | Subject 1 | Subject 2 | Subject 3 | Subject 4 | Subject 5 | Average |
|---|---|---|---|---|---|---|---|---|
| Aroma intensity evaluation | Heating tool 2-1 | Chamomile | 4 | 4 | 4 | 3 | 4 | 3.8 |
|  | Heating tool 2-2 |  | 3 | 2 | 2 | 1 | 2 | 2.0 |
|  | Comparative heating tool 2 |  | 2 | 2 | 1 | 1 | 1 | 1.4 |
|  | Comparative heating tool 1 |  | 1 | 1 | 1 | 1 | 1 | 1.0 |

As can be clearly observed from the results shown in Table 2, sufficient aromatic properties were sustained in the heating tool 2-1 and the heating tool 2-2 even after storage. In contrast, more than half of the subjects evaluated the comparative heating tool 2 as odorless. Also with the comparative heating tool 1, all subjects evaluated the comparative heating tool 1 as odorless, and desirable aromatic properties were not obtained. All of them were confirmed as able to generate heat at a level sufficient for practical use, and provide sufficient heat keeping effect.

Example 3

Heating tools 3-1 to 3-5 were produced in a manner similar to that for the heating tool 1-1 of Example 1, except that, as a fragrance, not only chamomile (fragrance number: BR11880, manufactured by Ogawa & Co., Ltd.), but also Floral (fragrance number: BR12942, manufactured by Ogawa & Co., Ltd.), Rose (fragrance number: OFR3386, manufactured by T. Hasegawa Co., Ltd.), Fruity (fragrance number: OFR3363, manufactured by T. Hasegawa Co., Ltd.) or Soap (fragrance number: BR3906, manufactured by Ogawa & Co., Ltd.) were used. As a fragrance, a heating tool containing chamomile was designated as the heating tool 3-1, a heating tool containing Floral was designated as the heating tool 3-2, a heating tool containing Rose was designated as the heating tool 3-3, a heating tool containing Fruity was designated as the heating tool 3-4, and a heating tool containing Soap was designated as the heating tool 3-5.

In Example 3, the outer bags were opened and the heating tools were removed therefrom before and after storage of the respective heating tools, and the intensities of the aroma, changes in the aromatic notes, temperature, and duration time were evaluated for the respective heating tools. More specifically, the air-impermeable outer bags were opened, and five subjects were asked to smell the aroma of the respective heating tools removed from the outer bags before storage (24 hours after the production), evaluate the intensities of the aroma in a manner similar to that described above on a scale of 1 to 5, and evaluate the temperature one hour after the outer bags were opened. The heating tools were stored in a thermostatic chamber in the presence of oxygen at 50° C. for 30 days, and then the outer bags were opened similarly, the intensities of the aroma and the temperature one hour after opening were evaluated similarly, while the changes in the aromatic notes and duration time were also evaluated. As described above, the higher the value of the intensity of the aroma, the better the evaluation and the more intense the remaining aroma. The changes in the aromatic notes were determined by asking five subjects to smell the aroma of the respective heating tools after the opening of the outer bags, and evaluate those on the scale described below. The lower the value, the smaller the change in the aroma before and after storage.

<Changes in Aromatic Notes>
1: No change
2: Slightly changed
3: Somewhat changed
4: Changed
5: Greatly changed The temperature one hour after the outer bag was opened is a value measured one hour after the opening of the outer bag by laying a predetermined underlay material and a covering material on a warming portion defined in JIS S4100 (2007), heating the warming portion to 30° C., and holding it within one degree of that temperature, while causing a heating tool left in an atmosphere having the same temperature as the ambient temperature to generate heat based on the method of use. The duration time is a value measured as the time (unit: hour) during which, after the air-impermeable outer bags of the respective heating tools have been opened after storage, the temperatures of the respective heating tools are held at 40° C. or higher. As described above, the storage conditions of placing the heating tools in the thermostatic chamber in the presence of oxygen at 50° C. for 30 days, correspond to storage at room temperature (25° C.) for 1.5 years.

TABLE 3

| | Before the storage | | 50° C., 30 days later | | | |
|---|---|---|---|---|---|---|
| Heating tool | Aroma intensity | Temperature | Aroma intensity | Change in aromatic note | Temperature | Duration time |
| Heating tool 3-1 | 4.6 | 55 | 4.6 | 2.0 | 55 | 14 |
| Heating tool 3-2 | 4.8 | 55 | 3.8 | 2.4 | 55 | 14 |
| Heating tool 3-3 | 4.4 | 55 | 4.0 | 2.0 | 55 | 14 |
| Heating tool 3-4 | 4.2 | 55 | 3.6 | 1.8 | 55 | 14 |
| Heating tool 3-5 | 5.0 | 55 | 4.6 | 1.6 | 55 | 14 |

As can be clearly observed from the results shown in Table 3, the intensities of the aroma of the heating tools after being stored at 50° C. for 30 days tend to be weaker than before storage, but sufficient aromatic properties were sustained even after storage. The changes in the qualities of aroma before and after storage also remained subtle, and no great change was observed. The heat generation temperatures of the respective heating tools were sufficiently high, i.e., 55° C., which remained unchanged before and after storage. Therefore, it was confirmed that heat keeping effects sufficient for a heating tool such as a so-called hand warmer can be obtained. Furthermore, the duration time of the predetermined temperatures of the heating tools was sufficiently long, i.e., 14 hours, demonstrating that they have sufficient temperature keeping duration time as heating tools.

Example 4

A test was performed in a similar manner to that in Example 3 except that charcoal (manufactured by Obayashi Sangyo Co., Ltd., product name: Subai, iodine adsorption: 63 mg/g, average particle diameter 200 μm, electrically non-conductive) was used instead of carbon black. As a fragrance, a heating tool containing chamomile was designated as a heating tool 4-1, a heating tool containing Floral was designated as a heating tool 4-2, a heating tool containing Rose was designated as a heating tool 4-3, a heating tool containing Fruity was designated as a heating tool 4-4, and a heating tool containing Soap was designated as a heating tool 4-5.

TABLE 4

| | Before the storage | | 50° C., 30 days later | | | |
|---|---|---|---|---|---|---|
| Heating tool | Aroma intensity | Temperature | Aroma intensity | Change in aromatic note | Temperature | Duration time |
| Heating tool 4-1 | 4.4 | 45 | 3.8 | 2.6 | 45 | 4.4 |
| Heating tool 4-2 | 4.4 | 45 | 3.6 | 2.8 | 45 | 4.4 |
| Heating tool 4-3 | 4.2 | 45 | 3.4 | 2.6 | 45 | 4.4 |

TABLE 4-continued

| | Before the storage | | 50° C., 30 days later | | | |
|---|---|---|---|---|---|---|
| | | | | Change in | | |
| Heating tool | Aroma intensity | Temperature | Aroma intensity | aromatic note | Temperature | Duration time |
| Heating tool 4-4 | 4.4 | 45 | 3.2 | 2.0 | 45 | 4.4 |
| Heating tool 4-5 | 4.6 | 45 | 4.0 | 2.2 | 45 | 4.4 |

As can be clearly observed from the results shown in Table 4, also in the case where charcoal was used, the intensities of the aroma of the heating tools after being stored at 50° C. for 30 days tend to be weaker than before storage, but sufficient aromatic properties were sustained even after storage. No great change was observed in the qualities of aroma before and after storage. The heat generation temperatures of the respective heating tools were as high as 45° C., which remained unchanged before and after storage, demonstrating that sufficient heat keeping effects as heating tools can be obtained. The duration time of the temperatures of the respective heating tools was as long as 4.4 hours, demonstrating that the heating tools have sufficient temperature keeping duration time as heating tools.

Example 5

The components of the exothermic composition and the fragrance were mixed in a manner similar to that in Example 3 to obtain a mixture. In this Example, however, the test was performed without using a water soluble salt (common salt), and the proportions of the iron powder, the carbon black, the water, the vermiculite, the water-absorbing resin, and the fragrance were 51 wt %, 20.4 wt %, 20.4 wt %, 5.1 wt %, 2.6 wt %, and 0.5 wt %, respectively. As a fragrance, a heating tool containing chamomile was designated as a heating tool 5-1, a heating tool containing Floral was designated as a heating tool 5-2, a heating tool containing Rose was designated as a heating tool 5-3, a heating tool containing Fruity was designated as a heating tool 5-4, and a heating tool containing Soap was designated as a heating tool 5-5.

TABLE 5

| | Before the storage | | 50° C., 30 days later | | | |
|---|---|---|---|---|---|---|
| | | | | Change in | | |
| Heating tool | Aroma intensity | Temperature | Aroma intensity | aromatic note | Temperature | Duration time |
| Heating tool 5-1 | 4.8 | 51 | 3.8 | 2.0 | 51 | 3.2 |
| Heating tool 5-2 | 4.8 | 51 | 3.6 | 2.4 | 51 | 3.2 |
| Heating tool 5-3 | 4.0 | 51 | 3.6 | 2.0 | 51 | 3.2 |
| Heating tool 5-4 | 4.4 | 51 | 3.6 | 2.0 | 51 | 3.2 |
| Heating tool 5-5 | 5.0 | 51 | 4.6 | 1.4 | 51 | 3.2 |

As can be clearly observed from the results shown in Table 5, even in the case where the water soluble salt was not used, the intensities of the aroma tend to be weaker after storage than before storage, but sufficient aromatic properties were sustained even after storage. The changes in the qualities of aroma before and after storage also remained subtle, and no great change was observed. The heat generation temperatures of the respective heating tools were a sufficiently high temperature, i.e., 51° C., which remained unchanged before and after storage, demonstrating that sufficient heat keeping effects as heating tools can be obtained. Furthermore, the duration time of the predetermined temperatures of the respective heating tools was also as long as 3.2 hours, demonstrating that the heating tools have sufficient temperature keeping duration time as heating tools.

Example 6

The components of the exothermic composition and the fragrance were mixed in a manner similar to that in Example 3, giving a mixture. In this Example, however, the test was performed without using a water-retaining agent (water-absorbing resin and vermiculite), and the proportions of the iron powder, the carbon black, the water, the common salt, and the fragrance were 54.1 wt %, 21.6 wt %, 21.6 wt %, 2.2 wt %, and 0.5 wt %, respectively. As a fragrance, a heating tool containing chamomile was designated as a heating tool 6-1, a heating tool containing Floral was designated as a heating tool 6-2, a heating tool containing Rose was designated as a heating tool 6-3, a heating tool containing Fruity was designated as a heating tool 6-4, and a heating tool containing Soap was designated as a heating tool 6-5.

TABLE 6

| | Before the storage | | 50° C., 30 days later | | | |
|---|---|---|---|---|---|---|
| | | | | Change in | | |
| Heating tool | Aroma intensity | Temperature | Aroma intensity | aromatic note | Temperature | Duration time |
| Heating tool 6-1 | 4.8 | 51 | 4.4 | 1.4 | 51 | 2.1 |
| Heating tool 6-2 | 5.0 | 51 | 4.0 | 1.4 | 51 | 2.1 |
| Heating tool 6-3 | 4.6 | 51 | 4.4 | 1.6 | 51 | 2.1 |
| Heating tool 6-4 | 4.4 | 51 | 4.0 | 1.6 | 51 | 2.1 |
| Heating tool 6-5 | 5.0 | 51 | 4.4 | 1.6 | 51 | 2.1 |

As can be clearly observed from the results shown in Table 6, even in the case where no water-retaining agent was used, the intensities of the aroma tend to be weaker after storage than before storage, but sufficient aromatic properties were sustained even after storage. No great change was observed in the qualities of aroma before and after storage. The heat generation temperatures of the respective heating tools were a sufficiently high temperature, i.e., 51° C., which remained unchanged before and after storage, demonstrating that sufficient heat keeping effects as heating tools can be obtained. Furthermore, the duration time of the predetermined temperatures of the respective heating tools was also as long as 2.1 hours, demonstrating that the heating tools have sufficient temperature keeping duration time as heating tools.

Example 7

The components of the exothermic composition and the fragrance were mixed in a manner similar to that in Example 3, giving a mixture. In this Example, however, the test was performed without using any water soluble salt (common salt) or water-retaining agent (water-absorbing resin and vermiculite), and the proportions of the iron powder, the carbon black, the water, and the fragrance were 55.3 wt %, 22.1 wt %, 22.1 wt %, and 0.5 wt %, respectively. As a fragrance, a heating tool containing chamomile was designated as a heating tool 7-1, a heating tool containing Floral was designated as a heating tool 7-2, a heating tool containing Rose was designated as a heating tool 7-3, a heating tool containing Fruity was designated as a heating tool 7-4, and a heating tool containing Soap was designated as a heating tool 7-5.

TABLE 7

| | Before the storage | | 50° C., 30 days later | | | |
|---|---|---|---|---|---|---|
| Heating tool | Aroma intensity | Temperature | Aroma intensity | Change in aromatic note | Temperature | Duration time |
| Heating tool 7-1 | 4.6 | 41 | 4.4 | 1.4 | 41 | 1.5 |
| Heating tool 7-2 | 4.8 | 41 | 3.8 | 1.4 | 41 | 1.5 |
| Heating tool 7-3 | 4.6 | 41 | 4.2 | 1.6 | 41 | 1.5 |
| Heating tool 7-4 | 4.2 | 41 | 4.2 | 1.6 | 41 | 1.5 |
| Heating tool 7-5 | 4.8 | 41 | 4.6 | 1.8 | 41 | 1.5 |

As can be clearly observed from the results shown in Table 7, the intensities of the aroma tend to be weaker than before storage, but sufficient aromatic properties were sustained even after storage even in the case where no water soluble salt or water-retaining agent was used. No great change was observed in the qualities of aroma before and after storage. The heat generation temperatures of the respective heating tools were as high as 41° C., which remained unchanged before and after storage, demonstrating that sufficient heat keeping effects as heating tools can be obtained. The duration time of the temperatures of the respective heating tools was as long as 1.5 hours, demonstrating that the heating tools have sufficient temperature keeping duration time as heating tools.

This Example differs from the aforementioned Example 5 in terms of the presence or absence of the water-retaining agent. Comparing these results, it was found that heat generation tends to occur at a higher temperature and the duration time tends to be longer in the heating tools 5-1 to 5-5 (containing water-retaining agent) when compared to the heating tools 7-1 to 7-5 (no water-retaining agent). Therefore, it was found that the water-retaining agent contributes to generating heat at a higher temperature and sustaining the temperature. This Example differs from the aforementioned Example 6 in terms of the presence or absence of the water-soluble salt. Comparing these results, it was also found that heat generation tends to occur at a higher temperature and the duration time tends to be longer in the heating tools 6-1 to 6-5 (containing water soluble salt) when compared to the heating tools 7-1 to 7-5 (no water soluble salt). Therefore, it was found that the water soluble salt contributes to generating heat at a higher temperature and sustaining the temperature. It was found from the results of this Example, Example 5, and Example 6 that the predetermined temperatures tend to be sustained for longer periods of time in the cases where the water-retaining agent was contained when compared to the cases where the water soluble salt was contained.

Example 8

A test was performed in a manner similar to that in Example 7 except for using, instead of the carbon black used in Example 7, a different type of carbon black (manufactured by Mitsubishi Chemical Corp., product name: HCF, iodine adsorption: 308 mg/g, average particle diameter: 0.016 electrically conductive). As a fragrance, a heating tool containing chamomile was designated as a heating tool 8-1, a heating tool containing Floral was designated as a heating tool 8-2, a heating tool containing Rose was designated as a heating tool 8-3, a heating tool containing Fruity was designated as a heating tool 8-4, and a heating tool containing Soap was designated as a heating tool 8-5.

TABLE 8

| | Before the storage | | 50° C., 30 days later | | | |
|---|---|---|---|---|---|---|
| Heating tool | Aroma intensity | Temperature | Aroma intensity | Change in aromatic note | Temperature | Duration time |
| Heating tool 8-1 | 4.4 | 42 | 2.8 | 1.8 | 42 | 2 |
| Heating tool 8-2 | 4.4 | 42 | 2.8 | 2.0 | 42 | 2 |
| Heating tool 8-3 | 4.6 | 42 | 2.6 | 1.6 | 42 | 2 |
| Heating tool 8-4 | 4.4 | 42 | 2.6 | 1.6 | 42 | 2 |
| Heating tool 8-5 | 5.0 | 42 | 3.6 | 1.8 | 42 | 2 |

As can be clearly observed from the results shown in Table 8, sufficient aromatic properties were sustained even after storage also in this Example where no water soluble salt or water-retaining agent was used. No great change was observed in the qualities of aroma before and after storage. The heat generation temperatures of the respective heating tools were a sufficiently high temperature, i.e., 42° C., which remained unchanged before and after the storage, demonstrating that sufficient heat keeping effects as heating tools can be obtained. Furthermore, the duration time of the predetermined temperatures of the respective heating tools was also sufficiently long, i.e., 2 hours, demonstrating that the heating tools have sufficient temperature keeping duration time as heating tools.

Example 9

A test was performed in a manner similar to that in Example 7 except for using, instead of the carbon black used in Example 7, a different type of carbon black (manufactured by Mitsubishi Chemical Corp., product name: HCF, iodine adsorption: 400 mg/g, average particle diameter: 0.013 electrically conductive). As a fragrance, a heating tool containing chamomile was designated as a heating tool 9-1, a heating tool containing Rose was designated as a heating tool 9-2, a heating tool containing Fruity was designated as a heating tool 9-3, and a heating tool containing Soap was designated as a heating tool 9-4.

TABLE 9

| | Before the storage | | 50° C., 30 days later | | | |
|---|---|---|---|---|---|---|
| | | | | Change in | | |
| Heating tool | Aroma intensity | Temperature | Aroma intensity | aromatic note | Temperature | Duration time |
| Heating tool 9-1 | 4.2 | 42 | 1.8 | 1.6 | 42 | 2 |
| Heating tool 9-2 | 4.4 | 42 | 2.0 | 1.6 | 42 | 2 |
| Heating tool 9-3 | 4.4 | 42 | 2.0 | 1.6 | 42 | 2 |
| Heating tool 9-4 | 4.8 | 42 | 3.2 | 1.6 | 42 | 2 |

As can be clearly observed from the results shown in Table 9, sufficient aromatic properties were sustained even after storage also in this Example. No great change was observed in the qualities of aroma before and after storage. The heat generation temperatures of the respective heating tools were a sufficiently high temperature, i.e., 42° C., which remained unchanged before and after storage, demonstrating that sufficient heat keeping effects as heating tools such as so-called hand warmers can be obtained. Furthermore, the duration time of the predetermined temperatures of the respective heating tools was also sufficiently long, i.e., 2 hours, demonstrating that the heating tools have sufficient temperature keeping duration time as heating tools.

Example 10

A test was performed in a manner similar to that in Example 7 except for using not only carbon black (manufactured by Mitsubishi Chemical Corp., product name: RCF, iodine adsorption: 144 mg/g, average particle diameter: 0.075 μm, electrically conductive) but also activated carbon (Futamura Chemical Co., Ltd., product name: Taiko Kasseitan, iodine adsorption: 1050 mg/g, average particle diameter: 50 μm, electrically conductive). The proportions of the iron powder, the carbon black, the activated carbon, the water, and the fragrance were 55.3 wt %, 20.8 wt %, 1.3 wt %, 22.1 wt %, and 0.5 wt %, respectively. As a fragrance, a heating tool containing chamomile was designated as a heating tool 10-1, a heating tool containing Floral was designated as a heating tool 10-2, a heating tool containing Rose was designated as a heating tool 10-3, a heating tool containing Fruity was designated as a heating tool 10-4, and a heating tool containing Soap was designated as a heating tool 10-5. The iodine adsorption of the oxidation accelerator in each of these heating tools was about 200 mg/g.

TABLE 10

| | Before the storage | | 50° C., 30 days later | | | |
|---|---|---|---|---|---|---|
| | | | | Change in | | |
| Heating tool | Aroma intensity | Temperature | Aroma intensity | aromatic note | Temperature | Duration time |
| Heating tool 10-1 | 4.2 | 42 | 3.4 | 1.6 | 42 | 2 |
| Heating tool 10-2 | 3.8 | 42 | 3.0 | 2.0 | 42 | 2 |
| Heating tool 10-3 | 4.4 | 42 | 2.8 | 1.6 | 42 | 2 |
| Heating tool 10-4 | 4.0 | 42 | 3.0 | 1.6 | 42 | 2 |
| Heating tool 10-5 | 4.4 | 42 | 3.4 | 1.6 | 42 | 2 |

As can be clearly observed from the results shown in Table 10, sufficient aromatic properties were sustained even after storage also in this Example. No great change was observed in the qualities of aroma before and after storage. The heat generation temperatures of the respective heating tools were a sufficiently high temperature, i.e., 42° C., which remained unchanged before and after storage, demonstrating that sufficient heat keeping effects as heating tools can be obtained. Furthermore, the duration time of the predetermined temperatures of the respective heating tools was also sufficiently long, i.e., 2 hours, demonstrating that the heating tools have sufficient temperature keeping duration time as heating tools.

Example 11

A test was performed in a manner similar to that in Example 10 except for changing the amounts of the carbon black and activated carbon. The proportions of the iron powder, the carbon black, the activated carbon, the water, and the fragrance were 55.3 wt %, 15.9 wt %, 6.2 wt %, 22.1 wt %, and 0.5 wt %, respectively. As a fragrance, a heating tool containing chamomile was designated as a heating tool 11-1, a heating tool containing Floral was designated as a heating tool 11-2, a heating tool containing Rose was designated as a heating tool 11-3, a heating tool containing Fruity was designated as a heating tool 11-4, and a heating tool containing Soap was designated as a heating tool 11-5. The iodine adsorption of the oxidation accelerator in each of these heating tools was about 400 mg/g.

TABLE 11

| | Before the storage | | 50° C., 30 days later | | | |
|---|---|---|---|---|---|---|
| | | | | Change in | | |
| Heating tool | Aroma intensity | Temperature | Aroma intensity | aromatic note | Temperature | Duration time |
| Heating tool 11-1 | 4.2 | 50 | 2.4 | 1.6 | 50 | 3 |
| Heating tool 11-2 | 4.0 | 50 | 2.4 | 2.0 | 50 | 3 |
| Heating tool 11-3 | 4.2 | 50 | 2.0 | 1.6 | 50 | 3 |
| Heating tool 11-4 | 4.0 | 50 | 2.4 | 1.6 | 50 | 3 |
| Heating tool 11-5 | 4.4 | 50 | 3.0 | 1.6 | 50 | 3 |

As can be clearly observed from the results shown in Table 11, sufficient aromatic properties were sustained even after storage also in this Example. No great change was observed in the qualities of aroma before and after storage. The heat generation temperatures of the respective heating tools were a sufficiently high temperature, i.e., 50° C., which remained unchanged before and after storage, demonstrating that sufficient heat keeping effects as heating tools can be obtained. Furthermore, the duration time of the predetermined temperatures of the respective heating tools was also sufficiently long, i.e., 3 hours, demonstrating that the heating tools have sufficient temperature keeping duration time as heating tools.

Comparative Heating Tool 3

A test was performed in a manner similar to that in Example 10 except for not using carbon black. The proportions of the iron powder, the activated carbon, the water, and the fragrance were 55.3 wt %, 22.1 wt %, 22.1 wt %, and 0.5 wt %, respectively. As a fragrance, a comparative heating tool containing chamomile was designated as a comparative heating tool 3-1, a comparative heating tool containing Floral was designated as a comparative heating tool 3-2, a comparative heating tool containing Rose was designated as a comparative heating tool 3-3, a comparative heating tool containing Fruity was designated as a comparative heating tool 3-4, and a comparative heating tool containing Soap was designated as a comparative heating tool 3-5.

TABLE 12

| Comparative Heating tool | Before the storage | | 50° C., 30 days later | | | |
|---|---|---|---|---|---|---|
| | Aroma intensity | Temperature | Change in Aroma intensity | aromatic note | Temperature | Duration time |
| Comparative heating tool 3-1 | 4.0 | 51 | 1.0 | — | 51 | 3.2 |
| Comparative heating tool 3-2 | 3.4 | 51 | 1.0 | — | 51 | 3.2 |
| Comparative heating tool 3-3 | 3.6 | 51 | 1.0 | — | 51 | 3.2 |
| Comparative heating tool 3-4 | 4.0 | 51 | 1.0 | — | 51 | 3.2 |
| Comparative heating tool 3-5 | 4.6 | 51 | 1.0 | — | 51 | 3.2 |

As can be clearly observed from Table 12, it was confirmed that the comparative heating tools can also provide heat keeping effects sufficient for a heating tool, and had sufficient temperature keeping duration time. On the other hand, the intensities of the aroma were significantly lowered to odorless due to storage. Since the comparative heating tools became odorless, their changes in aromatic notes could not be evaluated.

Comparative Heating Tool 4

A test was performed in a manner similar to that in Example 10 except for changing the amounts of the carbon black and activated carbon in Example 10 and using chamomile as the fragrance. The proportions of the iron powder, the carbon black, the activated carbon, the water, and the fragrance were 55.3 wt %, 11 wt %, 11 wt %, 22.2 wt %, and 0.5 wt %, respectively. The iodine adsorption of the oxidation accelerator in the comparative heating tool 4 was about 600 mg/g.

TABLE 13

| Comparative Heating tool | Before the storage | | 50° C., 30 days later | | | |
|---|---|---|---|---|---|---|
| | Aroma intensity | Temperature | Change in Aroma intensity | aromatic note | Temperature | Duration time |
| Comparative heating tool 4 | 4.0 | 51 | 1.4 | 1.6 | 51 | 3.2 |

As can be clearly observed from Table 13, it was confirmed that this comparative heating tool can also provide heat keeping effects sufficient for a heating tool, and had sufficient temperature keeping duration time. In contrast, although no great change in aromatic notes caused by being stored was observed, the intensity of the aroma was significantly lowered due to storage.

Example 12

Figure 2:
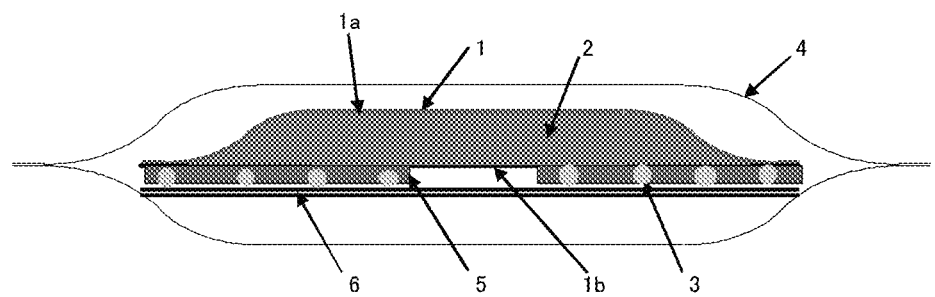
FIG. 2 shows an example of a stick-on type heating tool packaged in an outer bag. An air-permeable container bag illustrated in FIG. 2 is a model drawing of a container bag whose one side is an air-permeable portion and whose other side is an air-impermeable portion.
Figure 3:
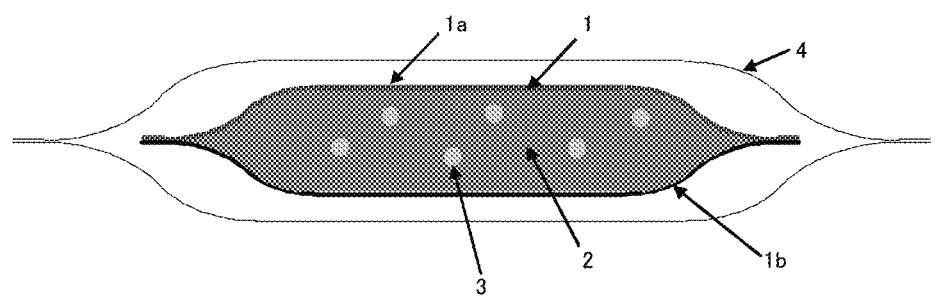
FIG. 3 shows an example of a heating tool packaged in an outer bag. An air-permeable container bag illustrated in FIG. 3 is a model drawing of a container bag whose one side is an air-permeable portion and whose other side is an air-impermeable portion.

Excellent aroma effects and exothermic effects were also obtained as mentioned above in the heating tools 1-1 to 1-3 and the heating tools 2-1 and 2-2 when the configuration of the heating tool shown in FIG. 2 or FIG. 3 was used instead of the configuration of FIG. 1.

DESCRIPTION OF THE REFERENCE NUMERALS

1. Air-permeable container bag (1a: air-permeable portion, 1b: air-impermeable portion)
2. Exothermic composition
3. Fragrance
4. Air-impermeable outer bag
5. Adhesive compound
6. Release paper

The invention claimed is:

1. A heating tool comprising:
   an exothermic composition containing an oxidation accelerator having an iodine adsorption of not higher than 250 mg/g, an oxidizable metal powder, and water; and
   a fragrance,
   wherein at least the exothermic composition is housed in a container bag having air permeability, the fragrance is contained in an amount of 0.0001 to 5 parts by weight per 100 parts by weight of the exothermic composition and the fragrance is contained in an amount of 0.01 to 50 parts by weight per 100 parts by weight of the oxidation accelerator in the exothermic composition.

2. The heating tool according to claim 1, wherein the exothermic composition further contains a water soluble salt and/or a water-retaining agent.

3. The heating tool according to claim 2, wherein the proportion of the oxidation accelerator in the exothermic composition is 1 to 30 wt %.

4. The heating tool according to claim 2, wherein the oxidation accelerator is at least one substance selected from the group consisting of carbon black, graphite, activated carbon, coal, charcoal, bamboo charcoal, acetylene black, and waste coffee grounds charcoal.

5. The heating tool according to claim 2, wherein the iodine adsorption of the oxidation accelerator is not higher than 200 mg/g.

6. The heating tool according to claim 2, wherein the oxidation accelerator has electrical conductivity.

7. The heating tool according to claim 2, wherein the fragrance is further housed in the container bag having air permeability.

8. The heating tool according to claim 2, wherein the fragrance is supported on a carrier.

9. The heating tool according to claim 1, wherein the proportion of the oxidation accelerator in the exothermic composition is 1 to 30 wt %.

10. The heating tool according to claim 1, wherein the oxidation accelerator is at least one substance selected from the group consisting of carbon black, graphite, activated carbon, coal, charcoal, bamboo charcoal, acetylene black, and waste coffee grounds charcoal.

11. The heating tool according to claim 1, wherein the iodine adsorption of the oxidation accelerator is not higher than 200 mg/g.

12. The heating tool according to claim 1, wherein the oxidation accelerator has electrical conductivity.

13. The heating tool according to claim 1, wherein the fragrance is further housed in the container bag having air permeability.

14. The heating tool according to claim 1, wherein the fragrance is supported on a carrier.

15. A use of, for producing a heating tool containing a fragrance, an exothermic composition containing an oxidation accelerator having an iodine adsorption of not higher than 250 mg/g, an oxidizable metal powder, and water, wherein the fragrance is contained in an amount of 0.0001 to 5 parts by weight per 100 parts by weight of the exothermic composition, and the fragrance is contained in an amount of 0.01 to 50 parts by weight per 100 parts by weight of the oxidation accelerator in the exothermic composition.

16. A method for sustaining aromatic properties derived from a fragrance in a heating tool containing the fragrance, by using an exothermic composition containing an oxidation accelerator having an iodine adsorption of not higher than 250 mg/g, an oxidizable metal powder, and water, wherein the fragrance is contained in an amount of 0.0001 to 5 parts by weight per 100 parts by weight of the exothermic composition, and the fragrance is contained in an amount of 0.01 to 50 parts by weight per 100 parts by weight of the oxidation accelerator in the exothermic composition.

* * * * *